(12) United States Patent
Meliti

(10) Patent No.: US 7,789,845 B1
(45) Date of Patent: Sep. 7, 2010

(54) SWAB/APPLICATOR FOR EAR CLEANING

(76) Inventor: Susan Meliti, 1134 Post Rd., Scarsdale, NY (US) 10583

( * ) Notice: Subject to any disclaimer, the term of this patent is extended or adjusted under 35 U.S.C. 154(b) by 103 days.

(21) Appl. No.: 11/705,691

(22) Filed: Feb. 13, 2007

Related U.S. Application Data

(60) Provisional application No. 60/814,803, filed on Jun. 20, 2006.

(51) Int. Cl.
A61F 13/15 (2006.01)
A41D 19/00 (2006.01)

(52) U.S. Cl. .............................. 604/1; 2/163

(58) Field of Classification Search ................ 604/1–3; 2/161.7, 163, 168
See application file for complete search history.

(56) References Cited

U.S. PATENT DOCUMENTS

| | | | | |
|---|---|---|---|---|
| 1,010,283 A | * | 11/1911 | Loy ................................ 2/163 |
| 1,200,596 A | * | 10/1916 | Daly .............................. 15/227 |
| 1,297,784 A | * | 3/1919 | Birnbaum ...................... 15/227 |
| 2,041,262 A | * | 5/1936 | Ness .............................. 15/188 |
| 2,075,681 A | * | 3/1937 | Welker ............................ 401/7 |
| 2,092,987 A | * | 9/1937 | Remington ................... 15/227 |
| 2,179,614 A | * | 11/1939 | Cohen ........................... 15/227 |
| 2,510,961 A | * | 6/1950 | Davis ............................. 604/1 |
| 2,599,191 A | * | 6/1952 | Meunier ..................... 15/167.1 |
| 2,686,325 A | * | 8/1954 | Silver ............................. 15/188 |
| 2,915,767 A | * | 12/1959 | Vaughan ..................... 15/167.1 |
| 2,925,605 A | * | 2/1960 | Wheeler ......................... 02/21 |
| 2,966,691 A | * | 1/1961 | Cameron ................... 15/104.94 |
| 3,043,295 A | * | 7/1962 | Ward ............................ 601/139 |
| 3,103,679 A | * | 9/1963 | Clemens .................... 15/167.1 |
| 3,368,668 A | * | 2/1968 | Micciche ..................... 206/229 |
| 3,626,946 A | | 12/1971 | Messey |
| 3,902,509 A | * | 9/1975 | Tundermann et al. ....... 433/142 |
| 3,905,113 A | * | 9/1975 | Jacob ........................... 433/216 |
| 3,982,298 A | * | 9/1976 | Ota ............................... 15/106 |
| 4,121,312 A | * | 10/1978 | Penney ......................... 441/57 |
| 4,308,860 A | * | 1/1982 | Sanders et al. .............. 601/137 |
| 4,335,731 A | * | 6/1982 | Bora, Jr. ...................... 433/216 |
| 4,616,374 A | * | 10/1986 | Novogrodsky ............. 15/167.1 |
| 4,617,694 A | * | 10/1986 | Bori ........................... 15/167.1 |
| 4,733,410 A | * | 3/1988 | Glotkin ............................ 2/21 |
| 4,884,581 A | * | 12/1989 | Rescigno .................... 128/869 |
| 4,920,974 A | * | 5/1990 | Roth et al. ................... 600/572 |
| 5,045,073 A | * | 9/1991 | Wagner ....................... 604/310 |
| 5,107,562 A | * | 4/1992 | Dunn ......................... 15/167.1 |
| 5,147,288 A | * | 9/1992 | Schiavo .......................... 604/1 |
| 5,213,428 A | * | 5/1993 | Salman .......................... 401/7 |
| 5,280,661 A | * | 1/1994 | Brown ........................... 15/214 |
| 5,320,531 A | * | 6/1994 | Delizo-Madamba ........ 433/136 |
| D363,606 S | * | 10/1995 | Abrahamson ............... D4/103 |
| D365,896 S | * | 1/1996 | Zuege .......................... D32/40 |
| 5,487,201 A | * | 1/1996 | Hansen et al. ........... 15/104.94 |
| 5,509,921 A | | 4/1996 | Karell |
| 5,604,952 A | * | 2/1997 | Zeleznick .................. 15/167.1 |
| 5,643,232 A | * | 7/1997 | Villotti, Jr. .................. 604/292 |
| 5,765,252 A | * | 6/1998 | Carr ......................... 15/104.94 |
| 5,807,301 A | * | 9/1998 | Nadam ............................ 604/1 |
| 5,819,765 A | * | 10/1998 | Mittiga ....................... 132/309 |

(Continued)

Primary Examiner—Tatyana Zalukaeva
Assistant Examiner—Paula L Craig

(57) ABSTRACT

The swab/applicator for removal of earwax and fluid from the ear canal and for applying medicines provides a flexible sleeve that fits over a person's finger, made of cotton, nylon, elastic, gauze. An absorbent tip is removably or permanently attached non-rigidly to the sleeve proximate the user's finger tip.

8 Claims, 3 Drawing Sheets

U.S. PATENT DOCUMENTS

| | | | |
|---|---|---|---|
| 5,826,599 A * | 10/1998 | Adams | 132/308 |
| 5,875,513 A * | 3/1999 | Reinold | 15/227 |
| 5,887,283 A * | 3/1999 | Mackay | 2/161.6 |
| 6,019,773 A * | 2/2000 | Denmark | 606/161 |
| 6,110,186 A * | 8/2000 | Rizvi | 606/148 |
| D447,298 S * | 8/2001 | Swoboda | D32/40 |
| 6,305,926 B1 * | 10/2001 | Ray | 425/458 |
| 6,432,117 B1 | 8/2002 | Murray | |
| 6,669,657 B1 * | 12/2003 | Ongwela | 601/134 |
| 6,772,465 B2 * | 8/2004 | Mehta | 15/106 |
| 6,829,802 B2 * | 12/2004 | McKenzie | 15/227 |
| 6,981,283 B2 * | 1/2006 | Kujawski | 2/161.6 |
| 7,012,169 B2 | 3/2006 | McDevitt et al. | |
| 7,020,898 B1 * | 4/2006 | Pucci et al. | 2/161.6 |
| 7,346,955 B2 * | 3/2008 | De Laforcade | 15/227 |
| 2003/0037389 A1 * | 2/2003 | Kuhr | 15/104.94 |
| 2005/0019083 A1 * | 1/2005 | Williams et al. | 401/7 |
| 2005/0071938 A1 * | 4/2005 | McDevitt et al. | 15/104.94 |
| 2005/0154342 A1 * | 7/2005 | Cynn | 604/1 |
| 2006/0137069 A1 * | 6/2006 | Yang et al. | 2/21 |
| 2006/0137070 A1 * | 6/2006 | Yang et al. | 2/21 |
| 2006/0242780 A1 * | 11/2006 | Yang et al. | 15/227 |
| 2006/0243295 A1 * | 11/2006 | Petit | 132/320 |

* cited by examiner

SWAB/APPLICATOR FOR EAR CLEANING

This application claims the benefit of provisional application No. 60/814,803 filed on Jun. 20, 2006.

BACKGROUND OF THE INVENTION

Two pieces of commonly-known advice are pertinent here: "Our fingers truly are the most versatile tools known to man." For young schoolchildren, "The only safe thing to put in your ear is your elbow." The reason for the second piece of advice is that an ear drum is easily damaged. Fortunately, the size of a person's fingers and the dimension of the ear's entrance way do not permit the fingers to reach as far in as to touch the ear drum, although long fingernails may still be a hazard to the ear drum. Among the more common reasons for an average person desiring to reach into the ear canal are removal of accumulated earwax, water after swimming or showering, soap and shampoo residues. Among the more common techniques used or devised by non-professional personnel to remove the undesired matter from the ear, are hand-held or hand-directed wads of absorbent cotton, toilet paper, napkins, rags, or cloth that are pushed into the ear and to some degree rotated. These devices may be reasonably effective in absorbing liquids but generally are ineffective in removing accumulated earwax. A problem may be exacerbated when wax is pushed further into the ear.

Frequently, and often unfortunately, rigid core extensions are provided for the person's fingers in the form of sticks, tweezers, nail files, toothpicks, all frequently wrapped with absorbent cotton and then inserted in the ear. Small diameter somewhat flexible rods covered at the ends with attached absorbent cotton form the well-known Q-tip.

These basically rigid extensions to the fingers are a real hazard to the eardrum when manipulated and maneuvered by persons not truly familiar with the ear's construction, or having unsteady hands. The extensions may be subject to vibrations or bumping, e.g., when in a moving vehicle, or by sudden movements by the subject (one person frequently performs ear cleaning on another, e.g., mother and child, hairdresser and customer). Lives become more difficult and unnecessarily more complicated when an eardrum has been punctured.

These are not hypothetical hazards. Rigid core or stick-based cotton-tipped applicators have been known to cause abrasions, scratches or damage to the ear canal or eardrum puncture. In addition cotton tips that are wrapped around rigid cores or sticks have detached inside the ear canal. Moreover, conventional rigid core or stick-based cotton-tipped applicators have been known to push wax and debris deeper into the ear canal, exacerbating the very problem they were intended to alleviate.

What is needed is a device for effectively cleaning or drying the accessible interior of the ear. The device should have a high degree of maneuverability like a person's finger and shall not include a rigidized extension that presents a hazard to the eardrum.

SUMMARY OF THE INVENTION

The swab/applicator of the present invention is a device that is effective in the safe removal of earwax and fluid from the ear canal and for applying medicines to the eyes, ears, nose, mouth, or any other orifice. The swab/applicator is comprised of a sleeve that fits over a person's finger or multiple fingers, made in different sizes, and made of cotton, nylon, elastic, gauze or any material, such as rubber or plastic. An absorbent tip made of absorbent cotton, sponge, or rubber, etc. is removably or permanently attached to the sleeve by stitching, gluing or other non-rigid method of attachment.

For people with long finger nails, additional protection is provided in an alternative embodiment by adding extra padding inside the sleeve adjacent the absorbent tip to prevent the nail from breaking through and becoming hazardous. The device is for a single use, or in alternative embodiments reused after cleansing, sanitizing, disinfecting or sterilizing. This swab/applicator may be pre-treated with medicine and sold in air-tight, sterile, sealed packages.

In summary, a swab/applicator in accordance with the invention provides a flexible sleeve that fits over a person's finger. A moisture-absorbent tip attaches to the sleeve's outer surface at the sleeve end adjacent to the person's fingertip. Thus, the absorbent tip becomes an extension of or adjunct or a person's finger and can be maneuvered by finger motion to extend farther into the ear than the finger itself. Insertion depth is nevertheless limited by the finger.

The tip is rotatable by rotating the finger. The tip may be short to entirely prevent contact with the eardrum when the finger/sleeve/tip assembly is inserted in the ear. Further, the tip may also extend within the sleeve to pad the fingernail of the user and provide additional isolation of the fingernail from inner surfaces of the ear. In a larger embodiment not for ear entry, the sleeve encloses more than one adjacent fingers and the absorbent tip is correspondingly widened.

The tip is absorbent, for example, fabricated of absorbent cotton, gauze, sponge, paper toweling, hydrophilic fibers, a porous pouch of hygroscopic material, or materials holding liquid by capillary action. For purposes of this Application an "absorbent tip" or "tip" is defined as a component of the invention which when brought into contact with a liquid or wet material, and is then withdrawn from contact, will engage and carry away at least a portion of the liquid or wet material.

The tip is usable as a swab or mop not only for ear cleaning. It may be used in many, many instances as an applicator of topical treatments. A pre-medicated tip may be packaged for sale in a sealed, sterile enclosure, with sleeve markings or selected coloring indicating the type of medication. In different embodiments, the tip may be permanently attached to the sleeve or may be replaceable. The swab/applicator and/or its absorbent tip may be capable of cleansing, reuse, and sterilization.

DESCRIPTION OF PREFERRED EMBODIMENTS

Figure 1:
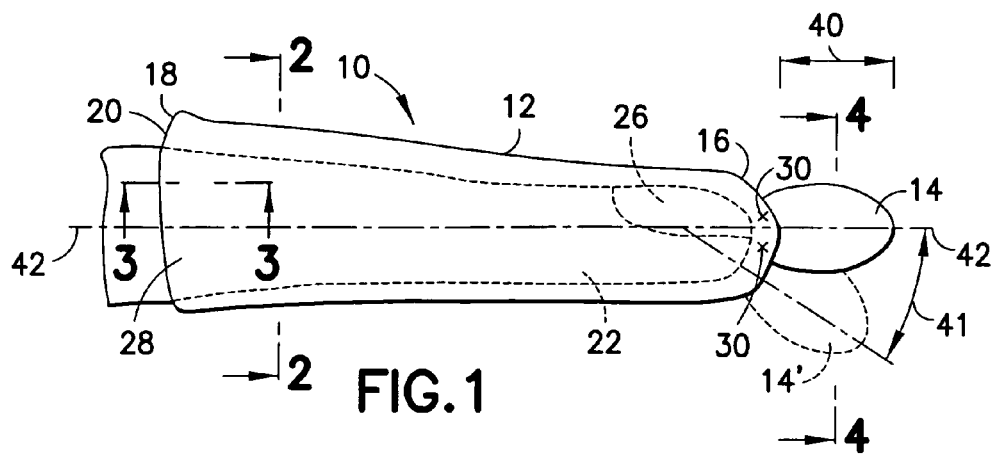
FIG. 1 is a side elevational view of a swab/applicator in accordance with the invention.
Figure 2:
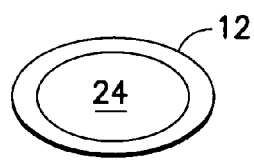
FIG. 2 is a sectional view taken along the line 2-2 of FIG. 1.
Figure 3:
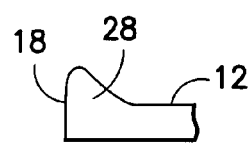
FIG. 3 is an enlarged sectional view taken along the line 3-3 of FIG. 1.
Figure 4A:
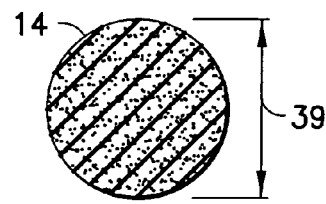
FIGS. 4a-4g are sectional views taken along the line 4-4 of FIG. 1.
Figure 4B:
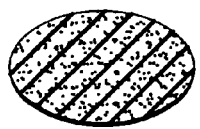
Figure 4C:
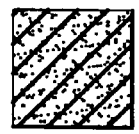
Figure 4D:
Figure 4E:
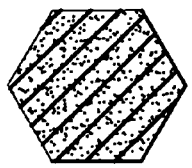
Figure 4F:
Figure 4G:
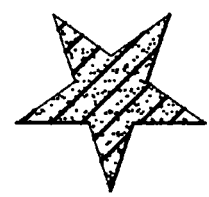

With reference to FIG. 1, a swab/applicator 10 in accordance with the invention includes a sleeve 12 of soft limp fabric, that is, not stiff or rigid. The fabric may be woven or non-woven and may be absorbent. An absorbent tip 14 connects to the sleeve 12 at the narrower closed-off end 16 of the sleeve 12. The other wider end 18 of the sleeve 12 defines an opening 20, thereby permitting insertion of a person's finger 22 into the tapering tunnel-like interior space 24 (FIG. 2) of the sleeve until the fingertip 26 contacts the sleeve end 16 internally and is able to direct force against the absorbent tip 14. A band or collar 28, an integral part of the sleeve 12, surrounds the opening 20, gives strength and definition to the end 18 and provides a closer fit with the finger 22. For this purpose the collar 28 may be elasticized in alternative embodiments. The tip 14 is absorbent cotton shaped like a truncated jellybean with cross-sections in the order of 0.25 to 0.75 inches diameter for human ear use (FIGS. 4a-g). Stitches 30 hold the tip 14 to the end 16 of the sleeve 12 in a non-rigid connection.

Figure 5:
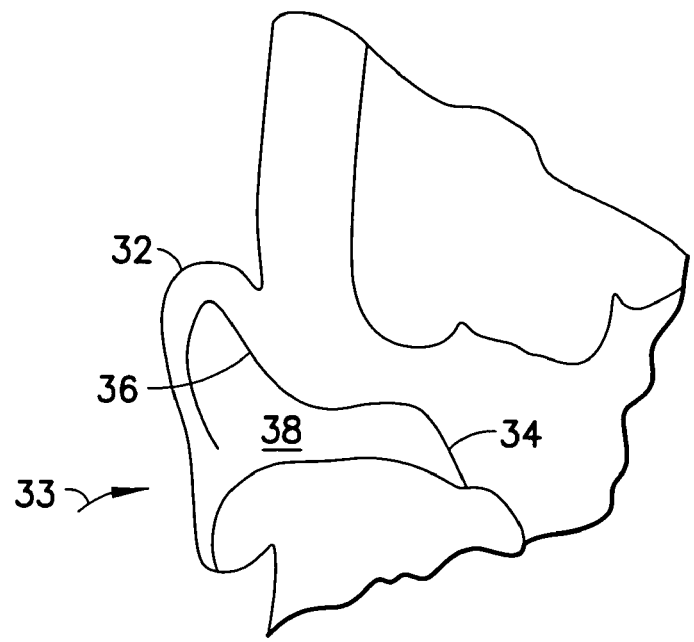
FIG. 5 is a simplified sectional view of the human ear.

To use this swab/applicator 10, the finger 22 is inserted into the sleeve opening 20 and the sleeve 12 is slipped over the finger until the finger position of FIG. 1 is achieved (approximately). Then, to draw moisture from or to clean an ear 32 (FIG. 5) the tip 14 is guided (arrow 33) by the finger 22, 26 through the ear entrance 36 to the ear canal 38 where the tip 14 may be brought into contact with the ear wall surfaces. The finger's cross-section and the extension 40 of the tip 14, in the order of 0.25 to 0.75 inch for the human ear, do not permit contact with the ear drum 34. (Note that none of the drawings is to a particular drawing scale and between different figures the scales may differ.) Rotative oscillation of the finger 22 produces similar motion of the tip 14.

The shapes of the tip are not limited to those shown in FIGS. 1 and 4. The cross-sections of the tip (FIGS. 4a-g) before insertion in the ear may be round 4a, oval 4b, square 4c, rectangular 4d, pentagonal 4e, or any polygonal shape 4f; the cross-section may be fluted 4g, etc., etc. A diameter of 0.75 inch before insertion was favorable with a soft sponge tip 14. The profile of the tip (FIG. 1) may taper, flare, or be rectangular as it extends away from the fingertip 26; the end surface farther away from the finger 26 of the tip 14 may include a concavity (not shown).

The tip need not be a generally symmetrical extension of a generally linear finger axis 42 (FIG. 1) but the tip 14' may extend away at an angle 41 from the axis 42 as illustrated in FIG. 1 with broken lines.

The tip 14, 14' may be permanently attached to the sleeve 12 as by the stitches 30, glue, etc., or removably attached by an adhesive, snapper, Velcro, pop-it bead-type connector, etc. The tip may be rotatable about the axis 42, for example, with a pop-it type connector. A rotatable tip may be connected for rotation to a hand-held motor and power supply by a thin flexible drive shaft (not shown) in a low power operation. A small motor (not shown) in the sleeve 12 may directly drive the tip in rotation or vibration. In such alternative embodiments, a battery contained in the motor, or hand held and connected to the motor by fine wires, may drive the motor.

Figure 6:
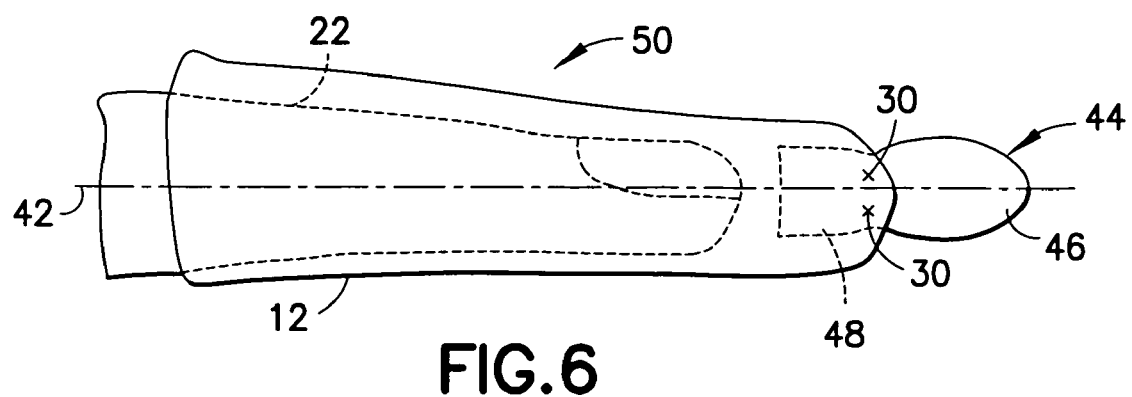
FIG. 6 is another embodiment of a swab/applicator in accordance with the invention.

FIG. 6 is an alternative embodiment 50 of a swab/applicator in accordance with the invention. Construction is the same as described in relation to FIGS. 1-4g except that the tip 44 extends into the sleeve 12 with an exterior portion 46 and an integral interior portion 48. The tip 44 is attached to the sleeve by stitches 30. The different means of attachment and alternative shapes of the tip portion 46 are as described above with reference to FIGS. 1-4g. The interior tip portion 48 isolates the finger 22 from the external tip portion 46 (and from the eardrum) and is a protection especially when the person has long finger nails. The sleeve may have a thin impermeable inner lining (not shown), for example, a lamination of rubber or synthetic rubber.

Figure 7:
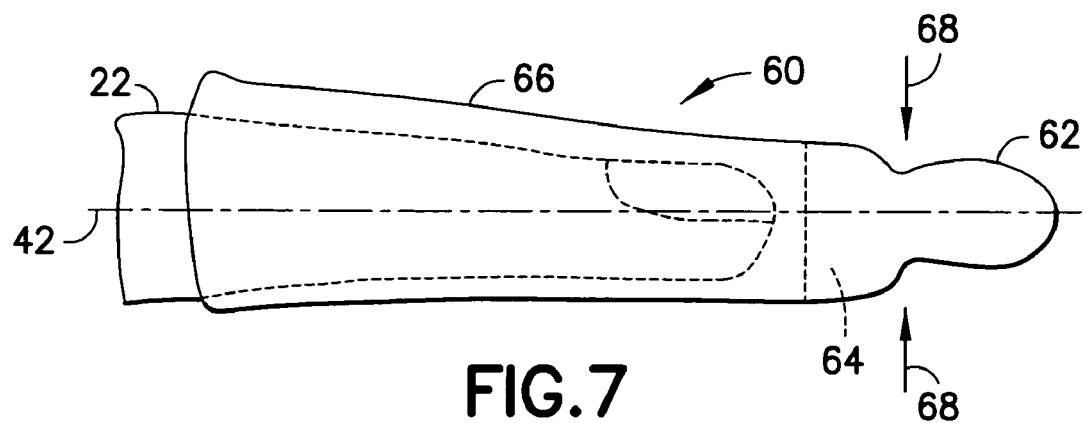
FIG. 7 is yet another embodiment of a swab/applicator in accordance with the invention.

In another embodiment 60 (FIG. 7) of a swab/applicator the sleeve material is absorbent or perforated so that moisture readily passes through at the closed end 62 where a mass 64 of absorbent material serves as an absorbent tip and is entirely within the sleeve 66. The closed sleeve end 62 is reduced in cross sectional area so as to serve as a swab for ear canal entry when a finger (that is too big in cross section to enter the ear canal) is in the sleeve.

Alternatively a closed tapering end of the sleeve may be pinched as indicated by the arrows 68 by external means (not shown), for example, by an elastic band or cord that produces a coke-bottle type necked-down profile. Stitching may also be used to define a closed end portion of the sleeve that includes an internal swab tip. Although the sleeve itself forms the basic enclosure for the absorbent material that constitutes a "tip", the "tip" is non-rigidly connected and is readily pivotable relative to the longitudinal finger axis 42 (as in the embodiments of FIGS. 1 and 6, for example). Separate external means for attaching a tip to a sleeve as in FIGS. 1 and 6 are unnecessary.

Thus, in three basic embodiments the tip is either (a) entirely external to the sleeve, (b) entirely internal to the sleeve, or (c) partially internal and partially external to the sleeve.

Figure 8:
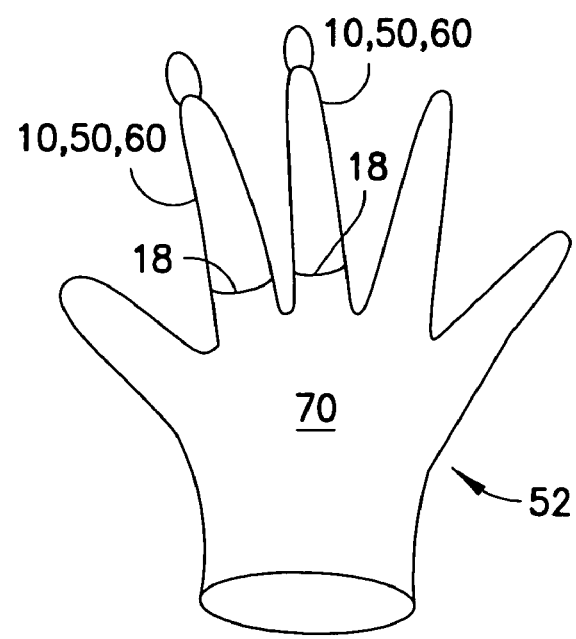
FIG. 8 is still another embodiment of a swab/applicator in accordance with the invention.

Each of the swab/applicators described above may be integral members of a full hand glove 52 where at least one finger, e.g., index and/or middle finger, of the glove is a swab/applicator 10, 50, 60. The open end 18 of the sleeve is attached to the palm/finger portion 70 of the hand glove (FIG. 8) with the internal space of the sleeve communicating with the internal space of the palm/finger portion. This arrangement protects the entire hand from contact with undesirable substances and surfaces and makes unintentional separation of the applicator from an active finger less likely. Alternatively the device can have fewer fingers; at least one sleeve/applicator is connected to the palm portion; the user's other fingers may remain exposed.

In all of the embodiments the sleeve length and cross sections may be made in different sizes to comfortably fit different hand sizes. Sleeve lengths when the swab/applicator is used by a person may extend from the finger tip to the region of the nearest knuckle joint, or to the mid knuckle joint, or to the finger joint proximate the person's palm.

The swab/applicator has many uses. For hobby and crafts, it can be useful for finger painting, maintenance and polishing of delicate objects; it can be used by scientists in laboratory work and experiments. In the beauty and cosmetics industry, the swab/applicator can apply or remove makeup and remove nail polish. In dermatology, the swab/applicator is useful for applying astringents, and other medications to the face. For infections, such as conjunctivitis, medication may be applied to the eyes. For colds, rubs may be applied to the outer portion of the nose and to the chest. For dryness or blistering around the mouth, petroleum jelly, creams and lotions may be applied. Ointments may be applied to any orifice of the body, including application of medicine to the ears.

The hands aided by the swab/applicator accomplish all these tasks, and at the same time, fingers and nails remain clean. The swab/applicator may also be effective for applying personal lubricants, used as an intimacy enhancer, or as an hygienic aid in insertion of suppositories and tampons. When used in conjunction with an impermeable lining such as rubber or used over a rubber glove, the swab/applicator can reduce risk of spreading germs or bacteria present on hands and finger nails and thus prevent infection of susceptible body areas. Further, since this the swab/applicator is absorbent it may be a welcome tool for surgeons and dentists. The swab/applicator is also effective for use by veterinarians for cleaning pets' ears, teeth and gums, for rectal examinations and insertion of medical devices into those orifices. The swab/applicator is useful by nurses, orderlies, and many other medical professionals. It is a suitable addition to a first aid kit. It is an aid in the treatment of diaper rash, cleaning a belly button, or cleaning and maintaining a colostomy or tracheotomy. There are many other uses for this device.

What is claimed is:

1. A swab/applicator for making contact with a selected area in the ear canal proximate the ear drum of an human ear, the selected area in the ear canal being unreachable by the finger of a user of the swab/applicator, consisting of:
   a single absorbent tip for contacting said selected area in the ear canal, said tip having a first end and terminating at a second end;
   a flexible elongated sleeve having a first end and a second end, said first end of said sleeve being closed and non-rigidly and permanently connected to said first end of said tip, said second end of said sleeve being open whereby in using said swab/applicator a person's finger may be inserted lengthwise into said second end of said sleeve, said tip providing a non-rigid extension to the length of the swab/applicator, and in use said tip providing a non-rigid extension to the length of the inserted finger, said tip being non-rigid over its entire length from said first to said second end and having a length in a range in the order of 0.30 inches to 0.75 inches, said tip having a dimensional cross-section that at its maximum is less than the cross section of the sleeve when a finger is inserted therein, said tip being able to reach the selected area in the ear canal proximate the ear drum.

2. A swab/applicator as in claim 1, wherein in use said tip at said first end of said sleeve is one of a longitudinal extension in length and an angled extension in length of the person's finger, said tip providing said non-rigid extension and having dimensions transverse to said length in a range in the order of 0.25 inches to 0.75 inches.

3. A swab/applicator as in claim 1, wherein said tip is constructed with at least one of absorbent cotton, sponge, paper toweling, gauze, hydrophilic fibers, hygroscopic material, and materials holding liquid by capillary action.

4. A swab/applicator as in claim 1, wherein a cross-section of said tip is at least one of square, polygonal and fluted.

5. A swab/applicator as in claim 1, said tip having a length; said first end of said sleeve being connected to said tip with a first portion of said tip length within said sleeve and with a second portion of said tip length external to said sleeve, whereby in using said swab/applicator a person's finger may be inserted lengthwise into said second end of said sleeve, said second portion of said tip external to said sleeve providing in use a non-rigid extension to the length of the finger, said first and second portions of said tip being of approximately equal lengths, said tip being able to reach the selected area in the ear canal proximate the ear drum.

6. A swab/applicator as in claim 5, wherein said tip is constructed with at least one of absorbent cotton, sponge, paper toweling, gauze, hydrophilic fibers, hygroscopic material, and materials holding liquid by capillary action.

7. A swab/applicator as in claim 5, wherein a cross-section of said tip is at least one of square, polygonal and fluted.

8. A swab/applicator as in claim 5, wherein in use said second portion of said tip external to said sleeve is one of a longitudinal extension in length and an angled extension in length of the person's finger, said second external portion of said tip having dimensions transverse to said length in a range in the order of 0.25 inches to 0.75 inches.

* * * * *